United States Patent
Wood et al.

(10) Patent No.: US 8,594,770 B2
(45) Date of Patent: Nov. 26, 2013

(54) MULTISPECTRAL DETECTION AND PRESENTATION OF AN OBJECT'S CHARACTERISTICS

(75) Inventors: Fred Wood, Medford, NY (US); Ron Goldman, Cold Spring Harbor, NY (US); Vincent Luciano, Shoreham, NY (US)

(73) Assignee: AccuVein, Inc., Huntington, NY (US)

( * ) Notice: Subject to any disclaimer, the term of this patent is extended or adjusted under 35 U.S.C. 154(b) by 359 days.

(21) Appl. No.: 12/925,166

(22) Filed: Oct. 14, 2010

(65) Prior Publication Data

US 2011/0112407 A1    May 12, 2011

Related U.S. Application Data

(63) Continuation-in-part of application No. 11/478,322, filed on Jun. 29, 2006, now Pat. No. 8,478,386, and a continuation-in-part of application No. 11/700,729, filed on Jan. 31, 2007, and a continuation-in-part of application No. 11/807,359, filed on May 25, 2007, now Pat. No. 8,489,178, and a continuation-in-part of application No. 12/215,713, filed on Jun. 27, 2008, and a continuation-in-part of application No. 11/823,862, filed on Jun. 28, 2007, now Pat. No. 7,983,738.

(60) Provisional application No. 61/278,948, filed on Oct. 14, 2009.

(51) Int. Cl.
*A61B 6/00* (2006.01)

(52) U.S. Cl.
USPC .......................... 600/476; 600/407; 600/473

(58) Field of Classification Search
USPC .......................... 600/407, 473, 476
See application file for complete search history.

(56) References Cited

U.S. PATENT DOCUMENTS

| | | |
|---|---|---|
| 3,818,129 A | 6/1974 | Yamamoto |
| 4,182,322 A | 1/1980 | Miller |

(Continued)

FOREIGN PATENT DOCUMENTS

| | | |
|---|---|---|
| FR | 2289149 | 5/1976 |
| GB | 1507329 | 4/1978 |

(Continued)

OTHER PUBLICATIONS

Chris Wiklof, "Display Technology Spawns Laser Camera," LaserFocusWorld, Dec. 1, 2004, vol. 40, Issue 12, PennWell Corp., USA.

(Continued)

*Primary Examiner* — James Kish
(74) *Attorney, Agent, or Firm* — Thomas A. O'Rourke; Bodner & O'Rourke, LLP

(57) ABSTRACT

An apparatus for capturing a multispectral image of an object is described. The apparatus includes one or more means for transmitting a beam of laser light at a first wavelength and a beam of laser light at one or more additional wavelengths different from the first wavelength. There is a means for causing the beams of laser light to travel in a coaxial path and a moving mirror. The beams of light bounce off the mirror thereby producing a two dimensional projection pattern. This pattern travels from the mirror along a first path to an object and wherein some of the laser light penetrates the object and travels to an internal structure of the object. The reflection of the laser light returns to a photo detector along a path different from said first path.

26 Claims, 10 Drawing Sheets

(56) References Cited

U.S. PATENT DOCUMENTS

| | | | |
|---|---|---|---|
| 4,265,227 A | 5/1981 | Ruge | |
| 4,312,357 A | 1/1982 | Andersson et al. | |
| 4,321,930 A | 3/1982 | Jobsis et al. | |
| 4,495,949 A | 1/1985 | Stoller | |
| 4,502,075 A | 2/1985 | DeForest et al. | |
| 4,619,249 A | 10/1986 | Landry | |
| 4,669,467 A * | 6/1987 | Willett et al. | 606/7 |
| 4,817,622 A | 4/1989 | Pennypacker et al. | |
| RE33,234 E | 6/1990 | Landry | |
| 5,214,458 A | 5/1993 | Kanai | |
| 5,261,581 A | 11/1993 | Harden | |
| 5,406,070 A | 4/1995 | Edgar et al. | |
| 5,423,091 A | 6/1995 | Lange | |
| 5,519,208 A | 5/1996 | Esparza et al. | |
| 5,541,820 A | 7/1996 | McLaughlin | |
| 5,542,421 A * | 8/1996 | Erdman | 600/477 |
| 5,603,328 A | 2/1997 | Zucker et al. | |
| 5,608,210 A | 3/1997 | Esparza et al. | |
| 5,631,976 A | 5/1997 | Bolle et al. | |
| 5,678,555 A | 10/1997 | O'Connell | |
| 5,772,593 A | 6/1998 | Hakamata | |
| 5,836,877 A | 11/1998 | Zavislan | |
| 5,860,967 A | 1/1999 | Zavislan et al. | |
| 5,969,754 A * | 10/1999 | Zeman | 348/136 |
| 5,982,553 A | 11/1999 | Bloom et al. | |
| 5,988,817 A | 11/1999 | Mizushima et al. | |
| 5,995,856 A | 11/1999 | Mannheimer et al. | |
| 6,032,070 A | 2/2000 | Flock et al. | |
| 6,056,692 A | 5/2000 | Schwartz | |
| 6,061,583 A | 5/2000 | Shihara et al. | |
| 6,135,599 A | 10/2000 | Fang | |
| 6,149,644 A | 11/2000 | Xie | |
| 6,178,340 B1 | 1/2001 | Svetliza | |
| 6,230,046 B1 | 5/2001 | Crane et al. | |
| 6,251,073 B1 | 6/2001 | Imran et al. | |
| 6,263,227 B1 | 7/2001 | Boggett et al. | |
| 6,334,850 B1 | 1/2002 | Amano et al. | |
| 6,424,858 B1 | 7/2002 | Williams | |
| 6,463,309 B1 | 10/2002 | Ilia | |
| 6,464,646 B1 | 10/2002 | Shalom et al. | |
| 6,542,246 B1 | 4/2003 | Toida | |
| 6,556,854 B1 | 4/2003 | Sato et al. | |
| 6,556,858 B1 | 4/2003 | Zeman | |
| 6,648,227 B2 | 11/2003 | Swartz et al. | |
| 6,689,075 B2 | 2/2004 | West | |
| 6,690,964 B2 | 2/2004 | Bieger et al. | |
| 6,702,749 B2 | 3/2004 | Paladini et al. | |
| 6,782,161 B2 | 8/2004 | Barolet et al. | |
| 6,882,875 B1 | 4/2005 | Crowley | |
| 6,889,075 B2 | 5/2005 | Marchitto et al. | |
| 6,913,202 B2 | 7/2005 | Tsikos et al. | |
| 6,923,762 B1 | 8/2005 | Creaghan, Jr. | |
| 6,980,852 B2 | 12/2005 | Jersey-Willuhn et al. | |
| 7,158,660 B2 | 1/2007 | Gee, Jr. et al. | |
| 7,225,005 B2 | 5/2007 | Kaufman et al. | |
| 7,239,909 B2 | 7/2007 | Zeman | |
| 7,247,832 B2 | 7/2007 | Webb | |
| 7,283,181 B2 | 10/2007 | Allen | |
| 7,333,213 B2 | 2/2008 | Kempe | |
| 7,359,531 B2 | 4/2008 | Endoh et al. | |
| 7,608,057 B2 | 10/2009 | Woehr et al. | |
| 2001/0056237 A1 * | 12/2001 | Cane et al. | 600/475 |
| 2002/0016533 A1 | 2/2002 | Marchitto | |
| 2002/0118338 A1 | 8/2002 | Kohayakawa | |
| 2003/0018271 A1 | 1/2003 | Kimble | |
| 2004/0022421 A1 | 2/2004 | Endoh et al. | |
| 2004/0171923 A1 | 9/2004 | Kalafut et al. | |
| 2005/0017924 A1 | 1/2005 | Utt et al. | |
| 2005/0043596 A1 | 2/2005 | Chance | |
| 2005/0047134 A1 | 3/2005 | Mueller et al. | |
| 2005/0113650 A1 | 5/2005 | Pacione et al. | |
| 2005/0135102 A1 | 6/2005 | Gardiner et al. | |
| 2005/0141069 A1 | 6/2005 | Wood et al. | |
| 2005/0143662 A1 * | 6/2005 | Marchitto et al. | 600/473 |
| 2005/0157939 A1 | 7/2005 | Arsenault et al. | |
| 2005/0161051 A1 | 7/2005 | Pankratov et al. | |
| 2005/0174777 A1 | 8/2005 | Cooper et al. | |
| 2005/0175048 A1 | 8/2005 | Stern et al. | |
| 2005/0215875 A1 | 9/2005 | Khou | |
| 2005/0281445 A1 | 12/2005 | Marcotte et al. | |
| 2006/0025679 A1 | 2/2006 | Viswanathan et al. | |
| 2006/0058683 A1 * | 3/2006 | Chance | 600/476 |
| 2006/0081252 A1 | 4/2006 | Wood | |
| 2006/0103811 A1 | 5/2006 | May et al. | |
| 2006/0122515 A1 | 6/2006 | Zeman | |
| 2006/0129037 A1 | 6/2006 | Kaufman et al. | |
| 2006/0129038 A1 | 6/2006 | Zelenchuk et al. | |
| 2006/0173351 A1 | 8/2006 | Marcotte et al. | |
| 2006/0232660 A1 | 10/2006 | Nakajima et al. | |
| 2006/0253010 A1 | 11/2006 | Brady et al. | |
| 2006/0271028 A1 | 11/2006 | Altshuler et al. | |
| 2007/0016079 A1 | 1/2007 | Freeman et al. | |
| 2007/0115435 A1 | 5/2007 | Rosendaal | |
| 2008/0045841 A1 | 2/2008 | Wood et al. | |
| 2008/0147147 A1 | 6/2008 | Griffiths et al. | |
| 2008/0194930 A1 | 8/2008 | Harris et al. | |
| 2010/0051808 A1 | 3/2010 | Zeman et al. | |
| 2010/0087787 A1 | 4/2010 | Woehr et al. | |
| 2010/0177184 A1 | 7/2010 | Berryhill et al. | |
| 2010/0312120 A1 | 12/2010 | Meier | |

FOREIGN PATENT DOCUMENTS

| | | |
|---|---|---|
| JP | 08023501 A | 1/1996 |
| JP | 2002328428 A | 11/2002 |
| JP | 2004/237051 | 8/2004 |
| JP | 2004237051 | 8/2004 |
| WO | WO 94/22370 | 10/1994 |
| WO | WO 96/39925 | 12/1996 |
| WO | WO 9826583 | 6/1998 |
| WO | WO 01/82786 | 11/2001 |
| WO | WO 03/009750 | 2/2003 |

OTHER PUBLICATIONS

Nikbin, Darius, "IPMS Targets Colour Laser Projectors," Optics & Laser Europe, Mar. 2006, Issue 137, p. 11.

* cited by examiner

MULTISPECTRAL DETECTION AND PRESENTATION OF AN OBJECT'S CHARACTERISTICS

CROSS-REFERENCE TO RELATED APPLICATIONS

This application claims priority on provisional patent application Ser. No. 61/278,948 filed Oct. 14, 2009, the disclosures of which are incorporated herein by reference. This application is a continuation in part of application Ser. No. 11/478,322, filed on Jun. 29, 2006 now U.S. Pat. No. 8,478, 386, U.S. patent application Ser. No. 11/700,729 filed Jan. 31, 2007 and U.S. patent application Ser. No. 11/807,359 filed May 25, 2007 now U.S. Pat. No. 8,489,178. This application is also a continuation in part of U.S. patent application Ser. No. 12/215,713 filed Jun. 27, 2008 and U.S. patent application Ser. No. 11/823,862 filed Jun. 28, 2007 now U.S. Pat. No. 8,478,386. All the foregoing disclosures are hereby incorporated by reference.

STATEMENT REGARDING FEDERALLY SPONSORED RESEARCH OR DEVELOPMENT (Not Applicable)

THE NAMES OF THE PARTIES TO A JOINT RESEARCH AGREEMENT (Not Applicable)

INCORPORATION-BY-REFERENCE OF MATERIAL SUBMITTED ON A COMPACT DISK (Not Applicable)

BACKGROUND OF THE INVENTION

1. Field of the Invention

The present invention relates to improvements in multispectral imaging for determining the characteristics of an objects, and more particularly to improvements which are capable of providing imaging of internal structure through trans-illumination apparatus and techniques.

2. Description of Related Art

The human visual system is able to detect light in a range of wavelengths that are typically described as "visible light." The longest wavelengths detected are red, the mid range is green and shortest wavelengths are blue. Long wavelength light such as infrared and short wavelength light such as ultraviolet are invisible to the human eye. The characteristics of an object that we can determine with the unaided eye are limited to those that can be detected in this spectrum. Furthermore, the trichromatic system used by the eye is broadband in nature and cannot see narrowband artifacts such as would be seen by a spectrophotometer.

Several products have reached market that emit infrared light on an object and use the reflected light to detect a pattern of varying contrast in the infrared spectrum. The device then projects an image that follows those contrast changes using a wavelength within the visible spectrum. In one such product, the AccuVein AV300, detects a pattern of absorption and reflection in the infrared and re-projects that pattern as red. Given that hemoglobin absorbs infrared light to a greater degree than the surrounding tissue, the projected pattern can be used by a medical practitioner to identify the position of a vein to be used for venipuncture.

In other products, the light is captured and the processed image is displayed on a remote screen such as an LCD panel or through an eyepiece that is in line with the object.

These contrast enhancement products act as color shifters. Just as the human eye would detect variations in absorption and reflection in the three colors it can see (red, green and blue), these contrast enhancers detect the variations at wavelengths outside the visible spectrum and display the corresponding pattern inside the visible spectrum.

OBJECTS OF THE INVENTION

1. It is an object of the invention to use a laser camera to detect characteristics of an observed object based on the reflection and absorption of the laser light or based on the re-emission of absorbed light at a different wavelength than the incident light.
2. It is an object of the invention to use a single or multiple wavelengths of laser light to detect characteristics of an observed object based on the reflection and absorption of the laser light based or the re-emission of absorbed light at a different wavelength than the incident light.
3. It is an object of the invention to use multi-spectral imaging by capturing light from wavelengths beyond just the visible light range, such as infrared and UV. This allows extraction of additional information that the human eye fails to capture with its receptors for red, green and blue.
4. It is an object of the invention to use hyper-spectral imaging by capturing information from a plurality of wavelengths including and beyond the visible light range, such as infrared and UV. This allows extraction of additional information that the human eye fails to capture with its broadband receptors.
5. It is an object of the invention to detect characteristics of the observed object both of the surface of the observed object when it its opaque and of the surface and below the surface when the object is translucent.
6. It is an object of the invention to improve the quality of detection of characteristics of the observed object by iteratively varying in real time the intensity of the light emitted by the laser camera based on the previously detected characteristics of the observed object
7. It is an object of the invention to present detected characteristics of the observed object back on to the object itself or on to a display visible to the user of the device or both using contrast, color, false color, icons or text or a combination of these modalities.
8. It is an object of the invention to capture detected characteristics of the observed object for the purpose of record keeping or for the purpose of post processing or for the purposes of detecting changes and trends in the observed object or a combination of these purposes.
9. It is an object of the invention to combine the detected characteristics of the observed object with external sources of data for the purposes of refining and/or extending the meaning of the detected characteristics.
10. It is an object of the invention to improve the detection characteristics of the system by using transillumination.
11. It is an object of the invention to detect characteristics of many types of objects and materials including veins, arteries, teeth, metals and plastics.

BRIEF SUMMARY OF THE INVENTION

The invention disclosed herein extends this concepts described in the parent applications in several novel ways, which can be used individually, or in combination.

1. By using more than one wavelength of light for analysis, additional characteristics about the object being scanned can be determined and then this additional information can be re-projected back on to the surface within the visible spectrum making these characteristics visible to a human either as a color-shifted image or as a false-color image. In this embodiment the device acts like a photo spectrometer that re-projects a visible image back on the object.
2. Contrast enhancement products rely on differential absorption and reflection of light (i.e. they detect contrast changes) and then re-project that contrast pattern. An alternative embodiment can also use florescence of the object being scanned by shining light of one wavelength on to the object and detecting light at another wavelength returned from the object and then this information being re-projected back on to the surface within the visible spectrum making these characteristics visible. In this embodiment the device acts like a spectroscope that re-projects a visible image back on the object.
3. This invention can further use florescence or color change of a material applied to the object being scanned that based on the characteristics of the object exhibits either a color change (and can therefore use contrast enhancement) or a florescence at one or more wavelengths of incident light.

The invention can be further enhanced by combining some or all of these techniques to detect and project different characteristics of the object being scanned and projecting them back on the object.

While many of the descriptions are for embodiments that use re-projection back on to the object under study as the user interface, embodiments with user interfaces remote from the object such as an LCD screen will be useful in many applications. Furthermore, the combination of re-projection and remote displays will also be useful in many applications.

While the devices and systems described herein focus on multispectral systems and describe specific embodiments of said devices and systems, the methods, features, functions, abilities, and accessories described in the parent applications apply fully.

DETAILED DESCRIPTION OF THE INVENTION

As is well known in the art, a laser camera works by emitting one or more laser beams and moving those beams in a pattern such that the beams cross over the area of an object of which an image is to be captured. A photo detector element in the camera captures the changes in light reflected from the object and uses that light change to create an image of the observed object. Note that as with a traditional camera, "object" should be read in this explanation as an object or as a group of objects (e.g., an apple or a still life that includes an apple). The pattern in which the beam is moved is unimportant as long as the position at which it strikes the object can be determined either directly or inferentially. Examples of patterns that can be used include raster and lissajous.

Figure 1:
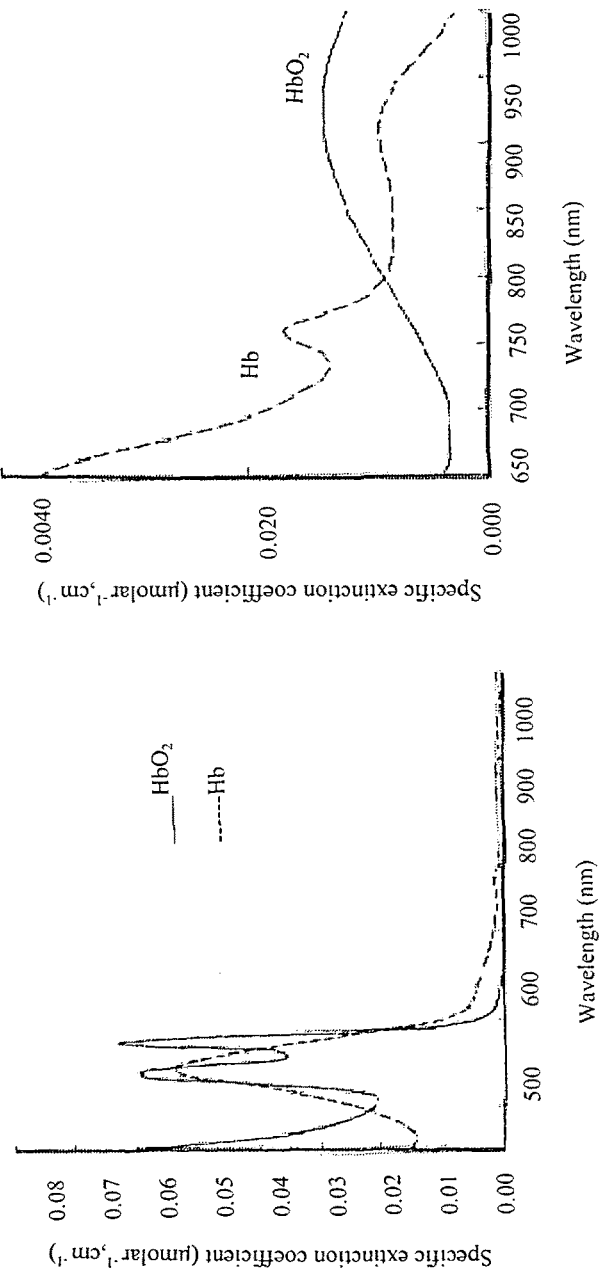
FIG. 1 shows the different absorption spectrum for deoxygenated human hemoglobin and for oxygenated hemoglobin.

As previously mentioned, the AccuVein AV300 is a laser camera system that uses a single infrared laser scanned over the object (in this case the human body) to determine the position of hemoglobin as a proxy for the position of a vein. The device uses the general characteristic of hemoglobin in that it absorbs infrared light to a greater degree than surrounding tissue. As seen in FIG. 1, there is a slightly different absorption spectrum for deoxygenated hemoglobin (as would be found in veins) and oxygenated hemoglobin (as would be found in arteries).

Through the addition of a second infrared laser of a different wavelength, or through the addition of a tunable laser allowing the wavelength to be changed, the invention could detect the difference between a vein and an artery. The user interface could then use one or more of several techniques to indicate the type of hemoglobin detected.

While a range of techniques could be used for the detection algorithm, in one embodiment the following truth table could be used:
1. Less reflection seen in either wavelength when compared to surrounding tissue? Position contains hemoglobin
2. Wavelength one reflection<wavelength two reflection? Position contains oxygenated hemoglobin
3. Wavelength one reflection>wavelength two reflection? Position contains deoxygenated hemoglobin Furthermore, a range of techniques could be used for the user interface. These include:
1. Project an image back on to the object that is scanned using a visible wavelength laser showing contrast changes between "hit" areas and surrounding areas
2. Project said areas using continuously variable brightness to track the contrast changes.
3. Project said areas using enhanced contrast to highlight the position of the detected hemoglobin
4. Project said areas using a color map (sometimes known as false color) where different colors represent different characteristics.

While the use of infrared wavelengths to detect different types of hemoglobin are used for this illustrative example, there are many characteristics well know in the art that can be determined by the absorption spectrum of an object that the invention would be equally suited to.

One embodiment of the invention uses a one or more data capture techniques as discussed previously and provides user feedback by re-projecting a re-colored image back on to the area being scanned. Since it is possible for one or more of the wavelengths of light being captured to overlap with the wavelengths of light being projected it is necessary to implement one or more techniques to prevent the projected light from being confused with the detected light.

These techniques include the following and can be combined:
1. Detect for a short period (e.g., a pixel time) and project for a short period.
2. Detect for a scan line and project for a scan line.
3. Detect for multiple scan lines and project for a scan line.
4. Detect for a scan line and repeat project for multiple scan lines.
5. Detect for a frame and project for a frame The illustrative uses of asymmetrical detection and projection allows a balance between the amount of time that might be needed for capture and the processing the captured information and the need to have a sufficiently high projection rate to provide a good user experience. Other asymmetrical combinations are possible.

An alternative embodiment of the invention is one in which diffuse light of one or more wavelengths is emitted and then reflected by the object under study. A digital camera using technology such as CMOS or CCD sensors captures an image of the object being studied to determine the reflection/absorption spectrum of the object. By controlling the emitted light wavelengths or by modifying the sensitivity spectrum of the image sensor, the spectral characteristics of the object can be determined.

Examples of modifying the response characteristics of the image sensor have been seen in the literature. For example, in "Laser Focus World" there is a discussion of a "CMOS imager with mosaic filter detects skin disorders" (http://www.laserfocusworld.com/articles/352154). Another related discussion is found at http://www.laserfocusworld.com/display article/368543/12/none/none/News/MEDICAL-IMAGING:-Real-time-multispectral-imager-promises-portable-diagnosi.

Transillumination

Figure 2:
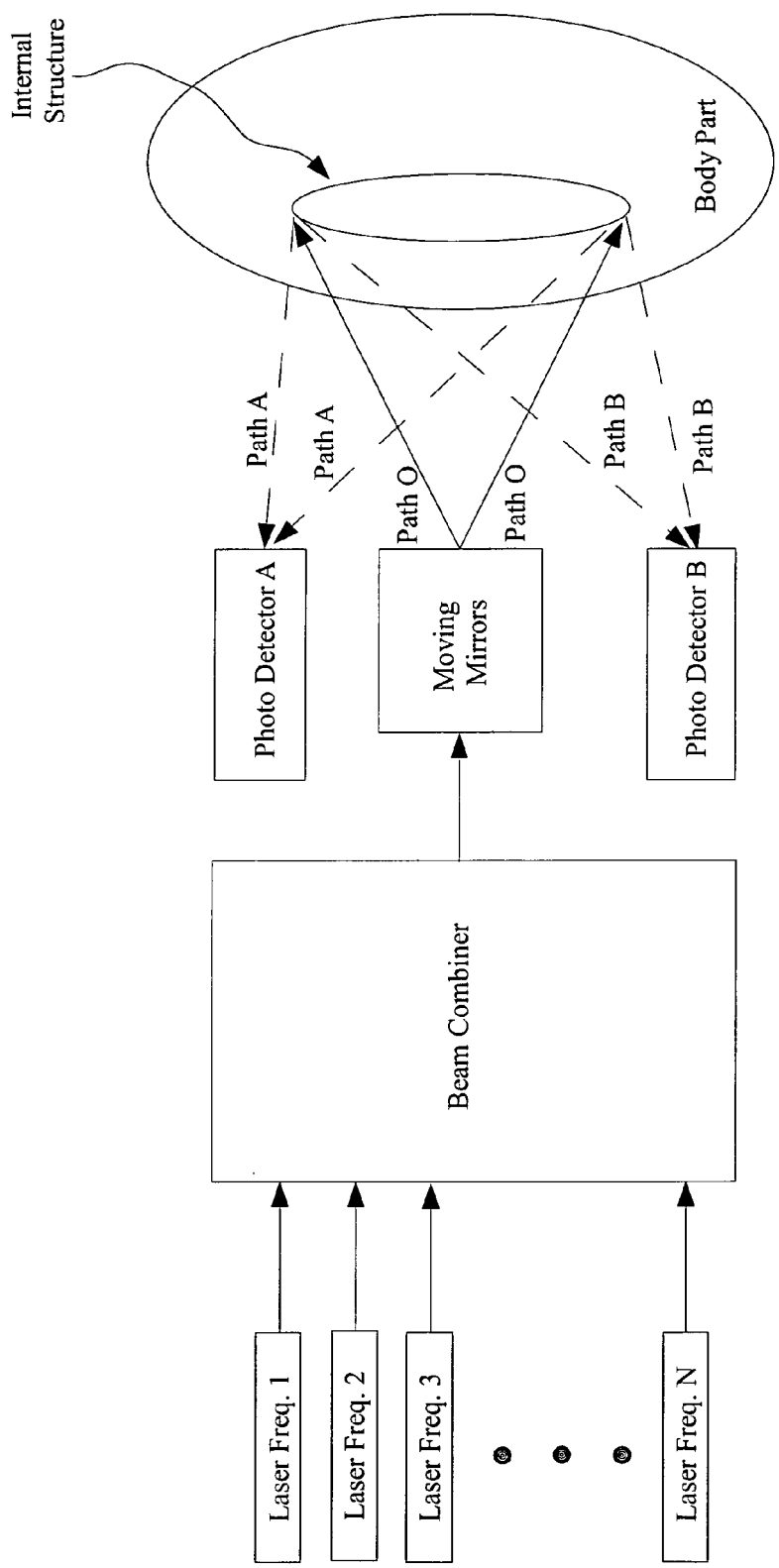
FIG. 2 shows a laser camera system having multiple frequency lasers for multispectral imaging applications.

FIG. 2 shows a laser camera having multiple frequency lasers for multispectral imaging applications. Multiple lasers (Laser Freq 1-Laser Freq N) are combined so that they are exiting coaxially from the Beam Combiner. They then bounce off a biaxial moving mirror (or a separate X and Y mirror) to produce a two-dimensional projection pattern. The pattern travels along Path O to a Body Part. Some of the Laser Freq wavelengths penetrate the Body Part and travel to the Internal Structure. The various Laser Freq wavelengths each interact with the internal structure in differing ways (varying levels of absorption and reflections). The reflections of the Laser Frequencies 1-N return to Photo Detector A and Photo Detector B along Path A and Path B respectively. The Photo Detectors may be, for example, a photo diode.

In one mode of operation, each Laser Freq 1-N is sequentially turned on for one frame of projection. The reflected light received at Photo Detectors A+B for that frame is then stored in a first frame memory location (not shown). In this manner, by sequentially stepping through Freq 1-N a multispectral image is stored in sequential frames of memory locations 1-N.

A characteristic of the system shown in FIG. 2 is that some portion of the projected Laser Freqs 1-N are reflected off the surface of the Body Part back to the Photo Detectors A+B. In the case where you are only interested in the characteristics of the Internal Structure, the reflections off the surface of the Body Part are essentially "noise" to the system. External structures, such a hair, scars, curvature of the body part, differences in reflectivity of exterior regions of the Body Part, all have the effect of generating noise that detract from imaging the Internal Structure. Algorithms can be written to help distinguish between the Internal Structure and the "noise", however, such algorithms are rarely perfect.

One method of penetrating deeper into the Body Part to see deeper Internal Structures is to increase the power output of the Lasers 1-N. However, as laser power is increased, the reflections off the external surface of the Body Part also increases. Eventually the Photo Detectors A+B, and the associated circuitry after them (not shown), gets saturated and the details of the Internal Structure get washed away.

Figure 3A:
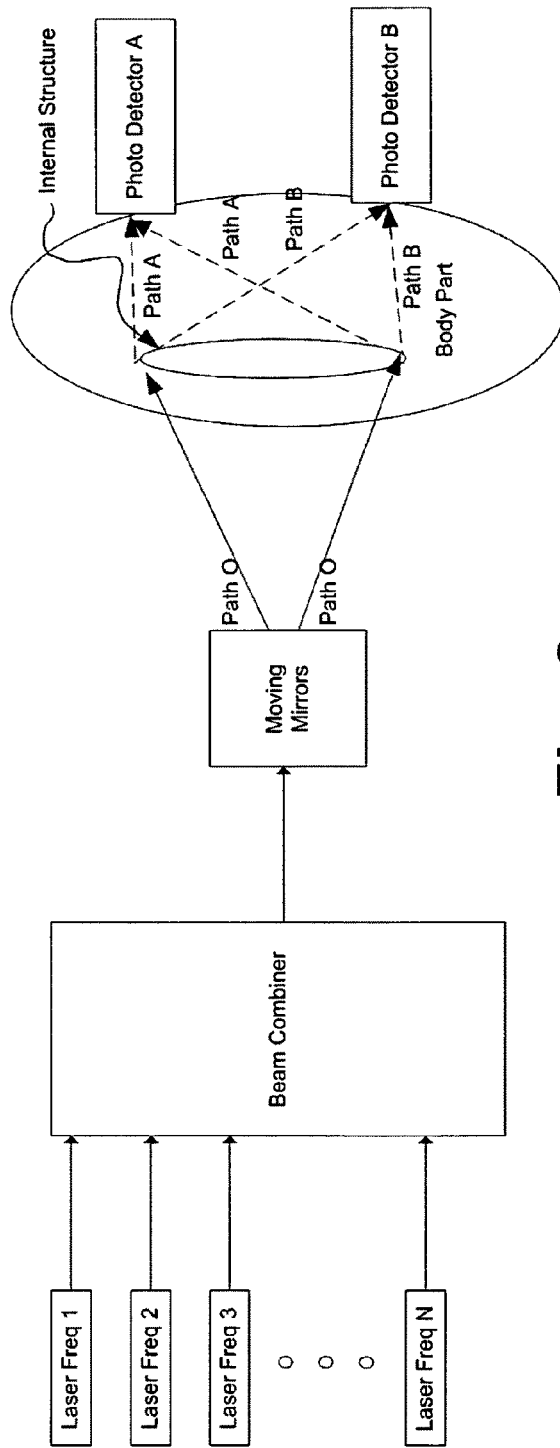
FIG. 3A shows the laser camera system of FIG. 2, but with a pair of photo detectors positioned to avoid laser light reflected from the skin surface, and positioned for transillumination of an internal structure.

FIG. 3A shows a system similar to that of FIG. 2 except that the Photo Detectors A and B are moved and are placed in a way that no light from lasers 1-N reflected from the surface of the skin can reach them. For example, they may be physically touching the skin of the Body Part (FIG. 3A). This type of system will be referred hereinafter as a transillumination laser system, wherein the Laser 1-N, upon hitting the Internal Structure, is then carried internal to the Body Part, with some portion of the light (shown as Path A and Path B) eventually hitting the Photo Detector A and/or B which are placed against the skin of the Body Part. Accordingly, the Laser Light that reaches Photo Detector A and/or B vary as a function of the Internal Structure's absorption and reflection of the Laser Light. For example, the presence of a highly absorptive tissue in the light path would decrease the signal generated by the Photo Detectors, while the presence of a highly scatterings tissue would increase it. It should be noted that the position of the Photo Detectors does not need to be on the side opposite the output laser Path O. The Photo Detectors can be placed anywhere on the Body Part, as long as sufficient internally carried light manages to reach the Photo Detectors.

Figure 3B:
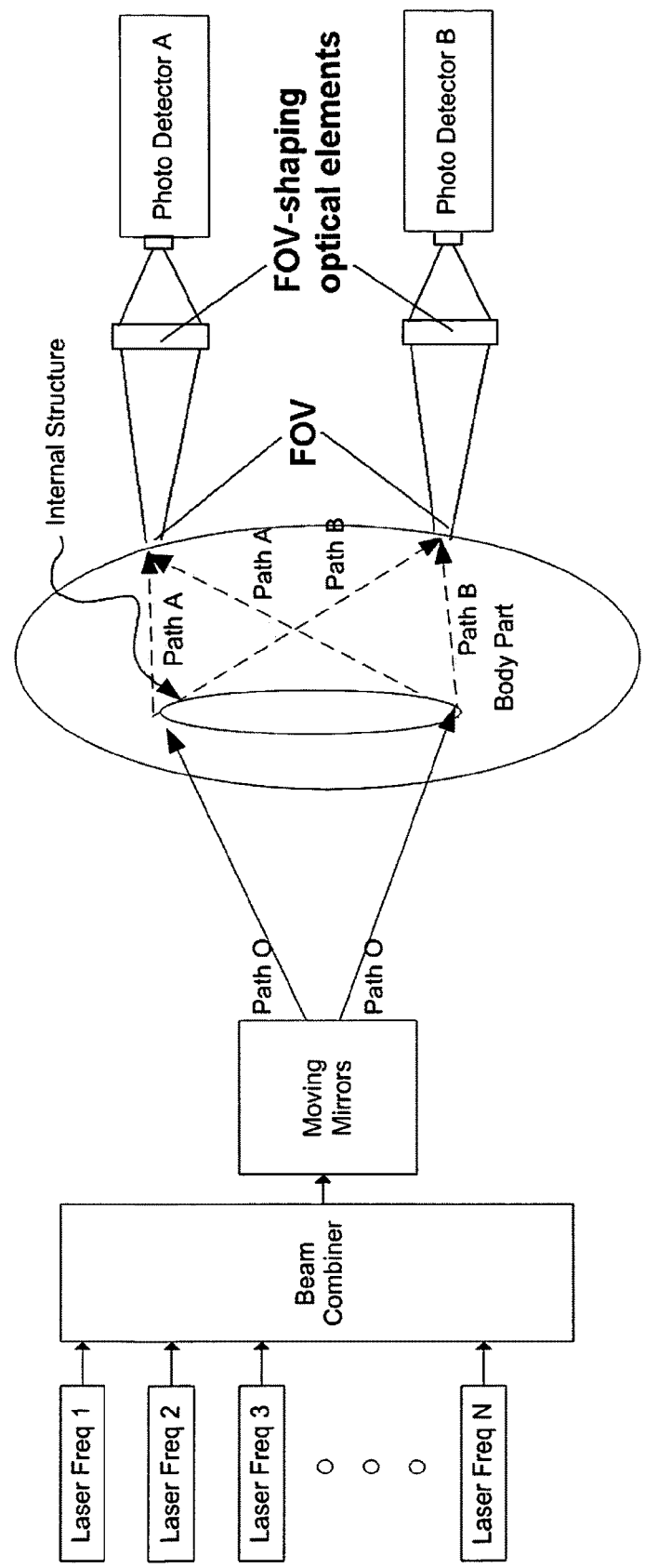
FIG. 3B shows the laser camera system of FIG. 3, but where the photo detectors are configured to have their field-of-view restricted by optical elements, to areas of the skin of the body part that are not directly illuminated by the laser light.

Nor do the Photo Detectors have to be physically touching the skin of the Body Part. Instead, they may configured to have their Field-of-View (FOV) restricted to areas of the skin the Body Part which are not directly illuminated by lasers 1-N (FIG. 3b). The FOV may be shaped by lenses, Fresnel lenses, curved mirrors or other optical elements. Additionally, the FOV of the Photo Detectors does not have to be stationary. Instead, it can be moving synchronously with the scanning system in such manner that no light from lasers 1-N reflected from the surface of the skin can reach them.

In the transillumination laser system of FIG. 3A/FIG. 3B, as the intensity of the Laser 1-N is increased, none of reflections off the surface of the Body Part are projected onto Photo Detector A or B. Accordingly, the power of Laser 1-N can be significantly increased to allow for imaging of deeper Internal Structures without concern for saturation due to reflections off the surface of the Body Part. Further, surface artifacts such as hair and surface blemishes are largely ignored. Essentially, the transillumination system allows for a greater signal to noise separation between the internal structure (the signal) and the reflections occurring off the surface of the Body Part (the noise). This allows for a much higher contrast ratio image of the underlying Internal Structure. In both FIGS. 2 and 3 individual Laser Freq 1-N were shown as individual blocks. It is also possible to purchase a tunable laser that can output a wide range of laser frequencies. This eliminates the need for the Beam Combiner of FIGS. 2 and 3A/3B. OpoTek Inc. sells a tunable laser system called the VIBRANT (HE) 355 II which can output frequencies in the range of 410-2400 nm. In such a case, the tunable laser will be set to a desired frequency for a single frame and the appropriate image captured. The tunable laser is set to the next frequency and its corresponding image is captured. This cycle repeats until all laser frequencies are cycled. This allows for a very large number of frequencies to be utilized.

Alternatively, a wide-band laser, which emits light of different wavelength simultaneously, may be used. Such lasers are known to be constructed with active media been confined to an optical fiber with various doping elements with overlapping emission spectra. Alternatively, the pulsed lasers with ultra-short pulses may be used where the spectrum is broadened by the sidebands of the frequencies associated with the pulse duration. One example of such lasers is a mode-locked laser.

In this case, different wavelengths will be detected by Photo Detectors with different spectral responses. In one embodiment, identical Photo Detectors with broadband response may have color filters which limit the response of each Detector to a narrow band of wavelengths (FIG. 9). Alternatively, the filters may be applied selectively, by moving or masking parts of the filter either mechanically (FIG. 9b). or electro-optically (FIG. 9 c), using electronically-controlled optical elements such as LCD shutters. Yet alternatively, color-resolved Detectors may be used, where the light of different wavelength is directed toward different detector elements by a grating or other suitable optical element (FIG. 9 d).

Figure 4:
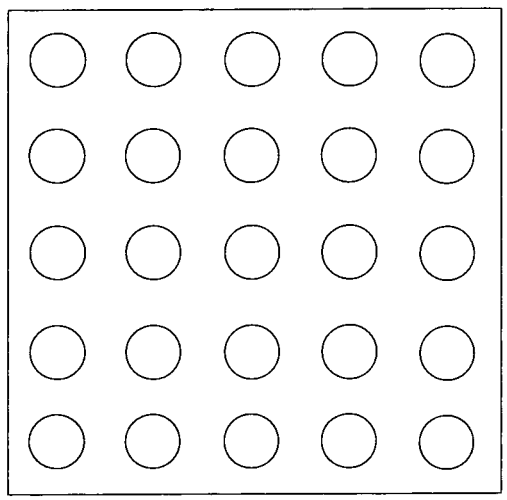
FIG. 4 shows a 5×5 array of photo detectors.

In a transillumination laser system, single, multiple, or arrays of Photo Detectors may be used instead of the two Photo Detectors shown in FIG. 3A/FIG. 3B. FIG. 4 shows a 5 by 5 array of Photo Detectors. This array of Photo Detectors is then placed in contact with the Body Part to receive the internally reflected Laser 1-N. In this embodiment the array can be placed anywhere on the Body Part except along optical Path O of FIG. 3A/FIG. 3B. A large array of Photo Detectors increases the photo detection area, thereby capturing more of the internally reflected light. Further, the Photo Detector array can uniformly distribute the receiving Photo Detectors over area so that it more uniformly receives the internally reflected light. In this manner, "hot spots" associated with fewer Photo Detectors can be minimized.

Figure 5:
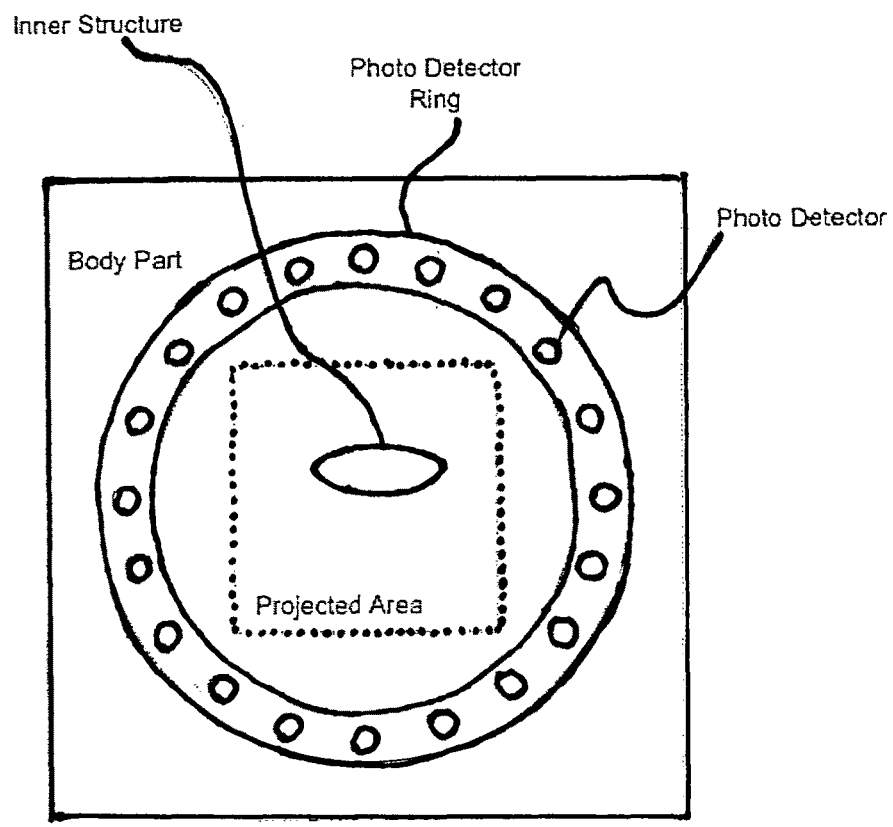
FIG. 5 shows a photo detector ring with a circular array of photo detectors arranged around the body part to be penetrated to detect laser light scattered from an inner structure.

FIG. 5 shows an embodiment wherein a Photo Detector Ring is placed around the Projected Area of the Laser 1-N. More specifically, it is a view from the perspective of the mirrors of FIG. 3. In this embodiment, the ring is placed against the surface of the Body Part in a position such that the Laser 1-N projected along Path O in FIG. 3A/FIG. 3B falls inside the inner edge of the Ring. The Lasers 1-N penetrates into the Body Part and interacts with the Inner Structure. The Lasers 1-N scatter inside the Body Part with a portion of the light being returned to the Photo Detector ring wherein it is detected. The detected light corresponds to the Inner Structure. In this embodiment, Lasers 1-N scattering off the surface of the Body Part do not reach the Photo Detectors on the Photo Detector ring, and therefore, do not interfere with the signal created when the Lasers 1-N interact with the Inner Structure. Accordingly, the power of the Lasers 1-N can be increased substantially to reach deeper Inner Structures without having the surface reflections creating "noise".

In FIGS. 2 to 6 the Photo Detectors are not shown with the electronics attaching them to a system. Such connectivity between the Photo Detectors and the system can be via a wired connection, a wireless connection, an optical connection, or any other transmission technique. Accordingly, a wide array of devices can be envisioned. For example, the Photo Detector array of FIG. 4 can be built into an armrest of a phlebotomy chair. In this case, when a person's arm is placed down on the armrest, the Photo Detectors are in contact with the skin. Alternatively, the photo array of FIG. 4 can be a wireless patch which gets affixed with some type of temporary adhesive to the body part and which wireless communicates the output of the Photo Detectors to the system.

The transillumination laser systems described herein can be utilized as a multispectral system for detecting bruising and erythema (which might indicate developing pressure ulcers). For example, article http://www.laserfocusworld.com/display_article/368543/12/none/none/News/MEDICAL-IMAGING:-Real-time-multispectral-imager-promises-portable-diagnosi describes a conventional CCD camera system for detection have a masked filter array for receiving images with the following frequencies of light 460, 525, 577 and 650 nm for detection of bruising or 540, 577, 650 and 970 for detection of erythema. However, such a system differs significantly from the transillumination laser system in that the CCD camera receives the light reflected off the skin, and therefore, does not have the same contrast ratio (or signal to noise performance) as transillumination laser system utilizing the same light frequencies for viewing events under the skin. Accordingly, a transillumination laser system utilizing the frequencies, for example 460, 525, 540, 577, 650 and 970 nm can be configured as described in FIGS. 3 to 6 for the detection of both bruising and erythema. The CCD camera system described is further limited in that the number of pixels of the CCD array gets reduced due to the masked filter. Accordingly, the density of the CCD imaging gets divided down by the number of frequencies in the mask. The laser system does not have this limitation in that a complete frame can be taken with each frequency of laser light.

While the laser system of FIG. 2 and the transillumination laser systems of FIGS. 3 to 5 have been herein describe with regard to multispectral laser systems, wherein more than one frequency of light is utilized, the transillumination described herein is applicable to the single frequency detection systems described in the parent applications hereto for the detection of blood vessels within a body.

Closed Loop Projection

Traditional CCD cameras have a large number of pixels that provide a high-resolution image. However, with conventional CCD cameras, each of the pixels has a common exposure time, and the camera lens typically has a single optical aperture setting per picture. Accordingly, it is very difficult to take a very good picture of a very bright item positioned very close to a very dim item. For example, if you were to attempt to take a picture of a seagull next to the sun, if you set the exposure time down (short) and/or the lens aperture opening so small (higher F number) that the sun does not saturate the CCD pixels, you could image the sun but the image of the seagull would be washed out. Conversely, if you set the exposure time long, and the lens aperture opened wide (smaller F number), you could image the bird but the sun would saturate the CCD pixels corresponding to it.

Figure 6:
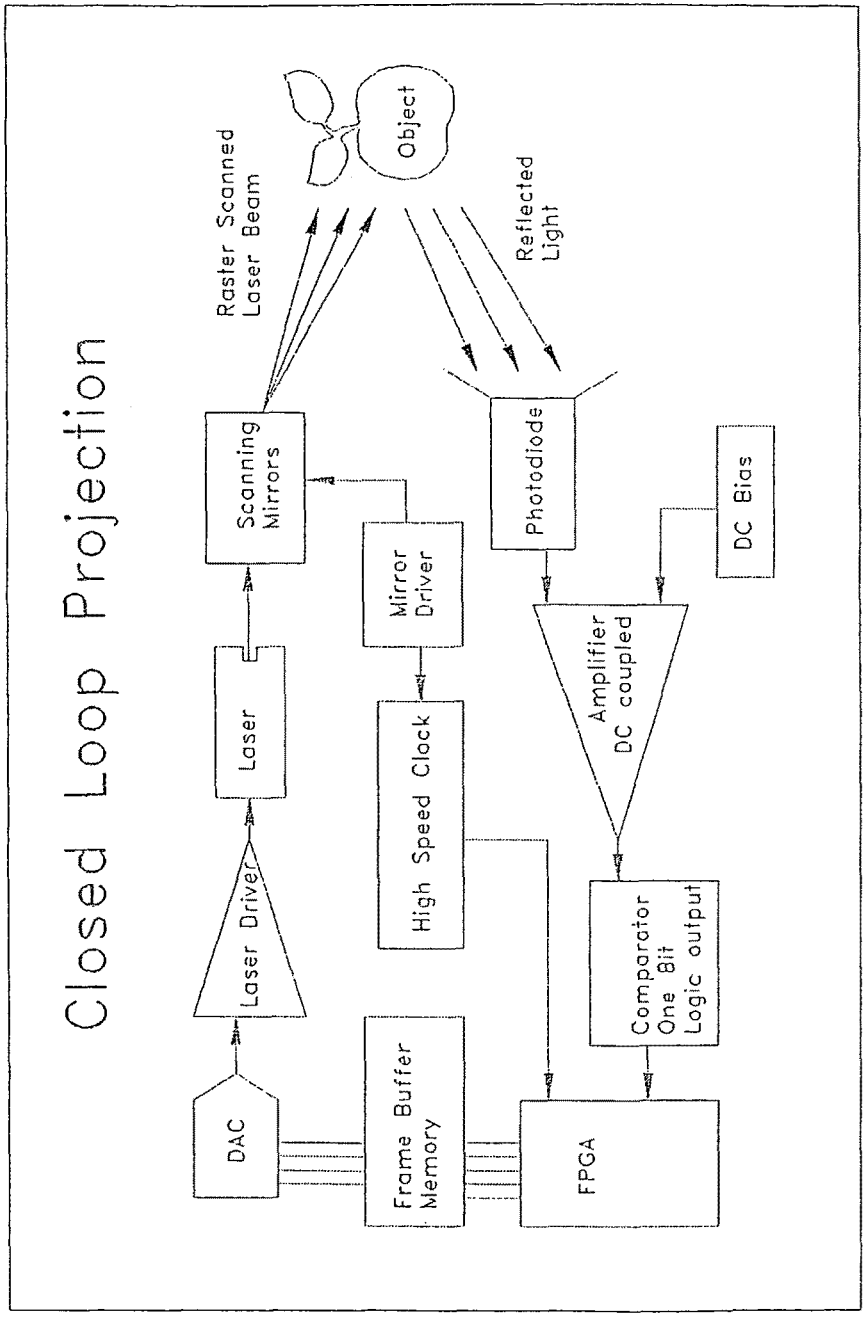
FIG. 6 shows a block diagram of a closed loop projection system capable of capturing images with high dynamic range.

Described in FIG. 6 is a closed loop laser imaging system that is capable of capturing images with very high dynamic range. In the parent application hereto, laser image capture systems are described in which the projected laser light is provided by a raster scanned laser beam. In FIG. 6, the laser, scanning mirrors, photo diodes, mirror drives can all be the same as previously described.

In FIG. 6 the laser beam brightness is controlled by a high speed DAC (digital to analog converter). This DAC is capable of varying the intensity of the laser at a very high rate (hundreds to thousands of times in each horizontal scan). Each segment of a duration corresponding to a desired resolution of the image will be referred hereafter as a pixel. Each pixel of the image has a memory location in the Frame Memory Buffer. Each pixel has a defined location on the object defined by a time slot in the frame.

A Photo Detector (or multiple Photo Detectors or Photo Detector array) receives the reflected light and provides a corresponding voltage to the Amplifier (DC coupled). The output is then provided to the Comparator (One Bit Logic Output) that in turn provides one bit of data. That one bit indicates whether the laser was "too bright" or "too dark" for that pixel. The result is then stored as Pixel brightness information and is updated with every frame. Stored pixel brightness is changed up or down depending on the Photo Detector bit. For maximum light contrast sensitivity, pixel data is always changed by at least one bit every frame. In this manner the closed loop projection image is constantly capturing.

Figure 7:
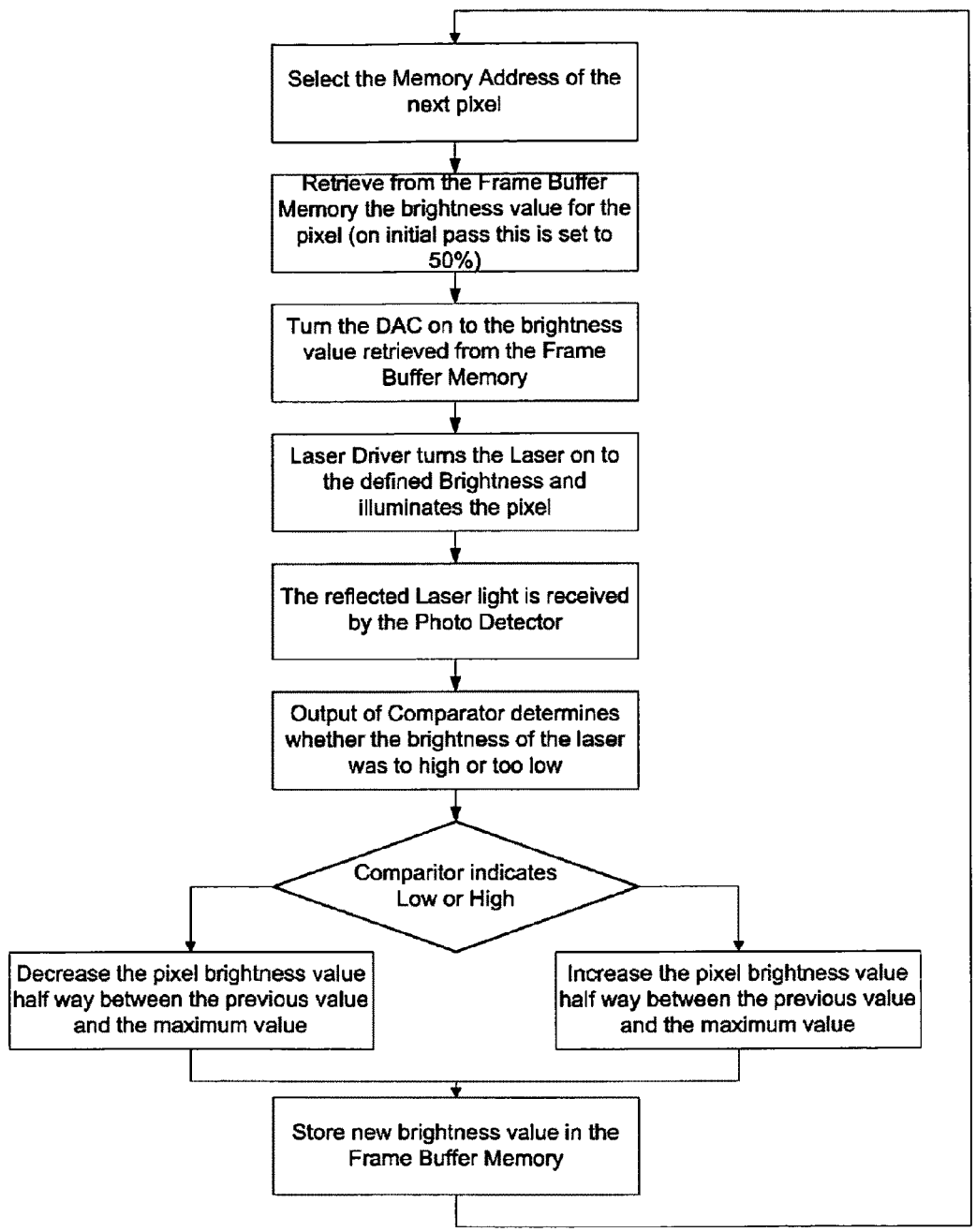
FIG. 7 shows a flow chart illustrating the functioning of the system of FIG. 6.

FIG. 7 is a flow chart illustrating the functioning of the system of FIG. 6.

Depending on the bits of brightness resolution, the system requires multiple frames to fully capture an image. For example, for 8 bits (255 shades), new image capture requires 8 frames. At 60 frames per second, that's 0.13 seconds to capture. After capture, image is maintained and updated with every frame. Since laser brightness (the DAC setting) is adjusted for each pixel, the reflected light for each pixel approaches one value. That value is the midpoint of the analog Photo Detector signal range. This scheme allows the highest contrast sensitivity and highest DC gain in the front end, because the analog signal approaches a flat line. Therefore the dynamic range of the system is not limited by the dynamic range or speed of the Photo Detector amplifier chain.

It is also possible to further increase the dynamic range and speed up the data acquisition of a closed loop laser imaging system by employing a fast, moderate resolution ADC in place of a single Comparator as described above, but still varying the laser power on a pixel-by-pixel basis to ensure nearly-uniform brightness of the resulting image. In this case, the dynamic range of the system would be generally equal to the product of the bit resolutions of the laser driver and the ADC, while the number of frames needed to capture a full-resolution image will be equal to a dividend of the bit resolutions of the laser driver and the ADC.

The time period during the top scan line of the image is reserved for Laser calibration. During calibration, the laser is driven to a defined maximum and then minimum brightness. During minimum brightness, the DC bias on the Photo Detector amplifier is adjusted to compensate for any change in ambient room lighting.

While FIG. 6 describes a system with a single laser, it is possible to implement a multiple laser system utilizing the closed loop projection method. Each frequency of laser can be sequentially cycled for a frame. Alternatively, multiple photo detectors can be filtered; each arranged to receive only one of the specific frequencies of laser light. In this manner, in each frame each frequency of light can concurrently be processed as shown in FIG. 6. For example, red, green and blue lasers can be utilized, wherein each color has a corresponding Frame Buffer Memory. This would function as a color image capture device. As a further example, a multispectral systems can be build, utilizing the frequencies described above for detection of bruising and erythema. Further, any frequencies of laser can be utilized provided that the photo detectors are capable of receiving such frequencies.

Additionally, the information captured at one wavelength may be used to adjust the laser power of different wavelength. Such wavelength cross-coupling may increase accuracy and/or shorten acquisition time of a multispectral closed loop laser imaging system.

The multispectral laser system FIG. 2, the Transillumination Laser System FIGS. 3 to 5 and the Closed Loop Projection system FIG. 6 can be combined together in a single system so that the advantages of each are provided.

Further, the concept described in the parent applications hereto of adding a visible laser as one of the Laser Freq 1-N can be applied to the multispectral laser system FIG. 2, the Transillumination Laser System FIGS. 3 to 5 and the Closed Loop Projection system FIG. 6.

Wherein it is described herein that the object is a Body Part, the multispectral laser system FIG. 2, the Transillumination Laser System FIGS. 3 to 5 and the Closed Loop Projection system FIG. 6 can be utilized on objects other than Body Parts. For example, they can be used on metals for detecting stress fractures, or can be used on plastic parts for detecting imperfections.

System for Evaluating Teeth

Figure 8:
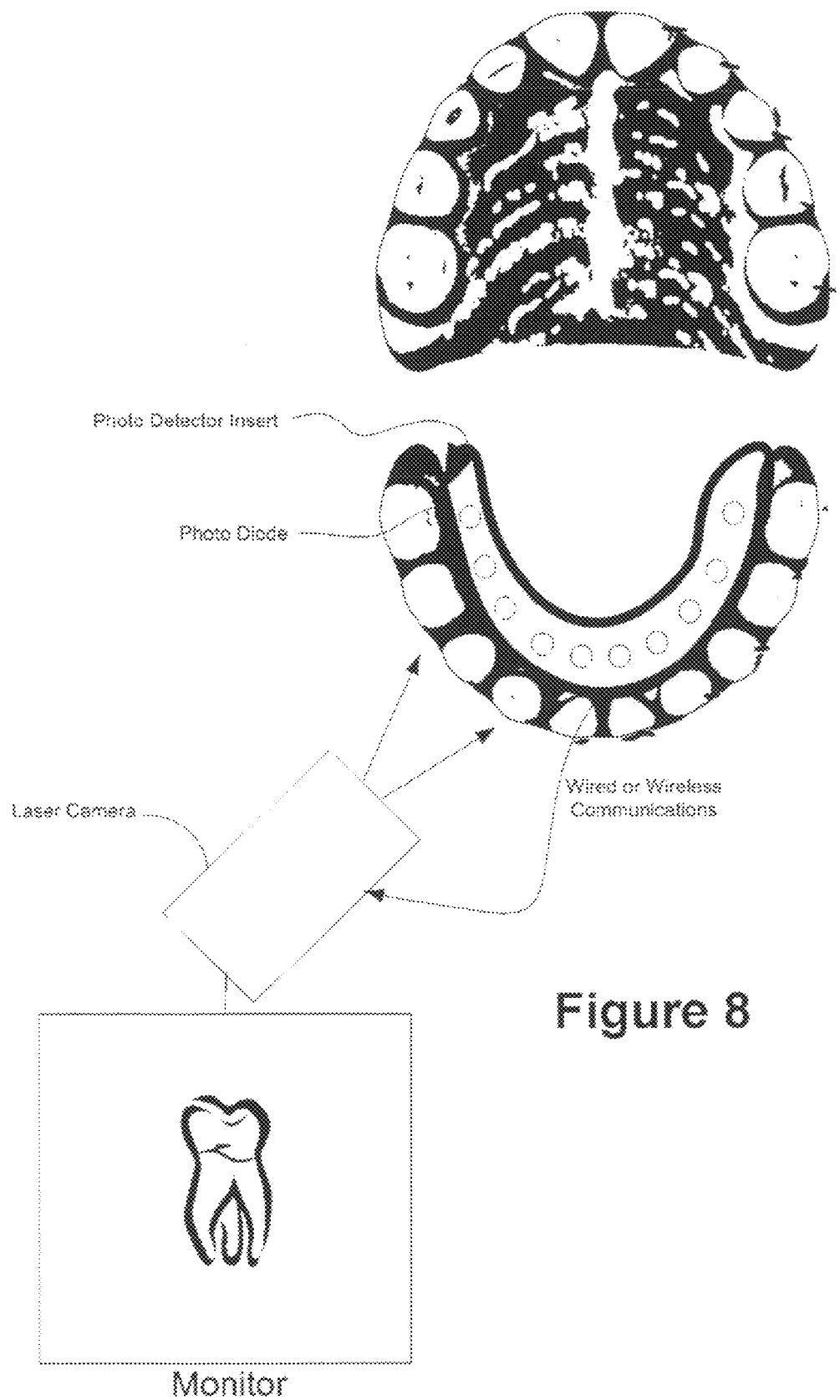
FIG. 8 shows a laser camera system for capturing images of a tooth.
Figure 9D:
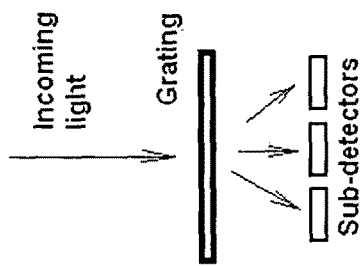
FIG. 9D shows a grating being used to transmit light to three different color-resolved detectors.
Figure 9C:
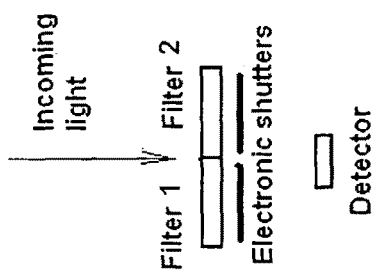
FIG. 9C shows the first and second filters of FIG. 9B with a pair of electronic shutters also being used to electro-optically limit the response of the photo detector.
Figure 9B:
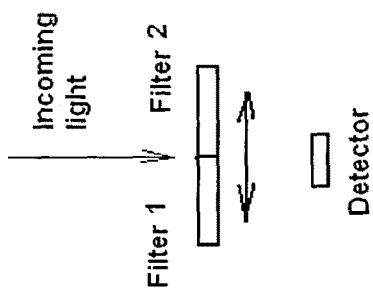
FIG. 9B shows a first filter and a second filter being used to limit the response of the photo detector.
Figure 9A:
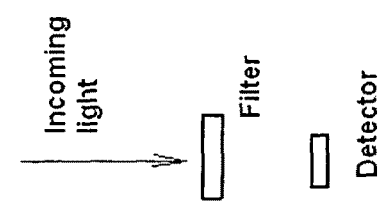
FIG. 9A shows a color filter which limits the response of the photo detector.

FIG. 8 shows a Laser Camera for capturing images of teeth. The Laser Camera can be designed as previously described in this application and the parent applications. A 1310 nm laser can be utilized as the laser source for imaging. It is known that the frequency of 1310 nm partially passes through teeth. The presence of cavity or other abnormalities will interfere with the reflection of the light. The laser light is transmitted in a raster pattern (or repetitive pattern) towards the teeth. Given that the tooth is relatively small, the laser beam is focused down to a very small spot size by the focusing lens within the Laser Camera. The maximum angle of the of transmitted pattern is made relatively small so that the light falls on a single tooth (or a small number of teeth).

The Laser Camera can be configured as a Transillumination Laser Camera, as previously described. A Photo Detector Insert, containing multiple Photo Diodes, can be placed inside the mouth of the patient and pressed against the backside of the teeth. The Photo Detector Insert will receive the laser light that is transmitted through the tooth. The Photo Detector Insert can be molded out of a transmissive gummy material so that it can slightly adhere to the backside of the teeth and provides an optical path for the 1310 nm light that scatters within the tooth and passes the light to the Photo Diodes. The light which is received by the Photo Detector Insert is converted to a signal (circuit not shown) which is then communicated (either wired or wirelessly) to the Laser Camera where the results are clocked into an image memory. Once a frame of data is clocked into an image memory it can then be output on a Monitor where the user can view the image of the teeth.

The Laser Camera can be designed as a closed loop imaging system as describe previously in FIGS. 6 and 7. Without the closed loop imaging system, if there are gaps between the teeth, the projected laser will pass through such gaps and saturate the Photo Detector Insert. The very high dynamic range provided by the closed loop imaging system will be beneficial in being able to pick out subtle details, such as cavities and cracks, that are directly next to the very bright spots caused by the gaps in the teeth. The laser power will be able to be substantially increased at specific pixels requiring more illumination, while being reduced requiring a lesser light source (such as the gaps in the teeth).

The Laser Camera can also be a multispectral camera as previously described, wherein the 1310 nm frequency is utilized with other frequency lasers for detecting other characteristics of the teeth.

We claim:

1. An apparatus for capturing a multispectral image of a deep internal structure of an object, said apparatus comprising:
   means to transmit a beam of light comprising two or more different wavelengths, said two or more different wavelengths configured to determine one or more characteristics of the internal structure;
   means to scan said beam of light in a plurality of optical paths to produce a two dimensional scan pattern;
   an array of photo detectors distributed around the object; each said photo detector configured to detect said scanned two or more wavelengths of light after being differentially absorbed by the internal structure and the surrounding areas, and to output a signal of a contrast formed by the absorption spectrum of said two or more wavelengths by the internal structure, said means to transmit further configured to also transmit one or more visible wavelengths of light, by using said signal from said photodetectors, to selectively project the one or more characteristics of the internal structure onto the surface of the object;
   a memory;
   a comparator configured to receive the output of said photo detectors, and to provide one bit of data for each pixel of the photo detector output to indicate whether its brightness is too bright or too dark, said bit of pixel brightness data being stored in said memory and being incrementally updated for said selective projection, said stored pixel brightness data used to adjust power to said means to transmit light, on a pixel-by-pixel basis, for said selective projection to provide improved contrast sensitivity for said projected image.

2. The apparatus according to claim 1 wherein said wherein said array of photo detectors comprises a ring of said photodetectors uniformly distributed around the object.

3. The apparatus according to claim 2 wherein each said photo detector comprises a respective optical element configured to shape a field of view of said respective photo detector.

4. The apparatus according to claim 1 wherein said selective projection comprises said means to transmit being configured to implement one or more techniques to alternate between differential absorption of said two or more wavelengths and said projection of said one or more visible wavelength.

5. The apparatus according to claim 4 wherein said one or more techniques comprises:
   said means to transmit configured to alternately scan only said two or more wavelengths for absorption for a specific period of time, and to project said one or more wavelengths for another specific period of time;
   said means to transmit configured to alternately scan a line and to project a line;
   said means to transmit configured to scan multiple lines and to project one scan line;
   said means to transmit configured to scan a line and repeatedly project for multiple scan lines; and
   said means to transmit configured to scan for a full frame and to project for a full frame.

6. The apparatus according to claim 1 wherein said selective contrast sensitivity of said projected image comprises said apparatus configured to project said two or more visible wavelengths using a color map, wherein each of said two or more wavelengths comprises a color configured to represent a different characteristic.

7. The apparatus according to claim 1 wherein said scanned two or more wavelengths comprise two or more hyper-spectral wavelengths of light.

8. The apparatus according to claim 1 wherein said means to transmit is configured to transmit a beam of light comprising six discrete wavelengths being 460 nm, 525 nm, 540 nm, 577 nm, 650 nm, and 970 nm, to thereby be configured to detect two characteristics, being bruising and erythema.

9. The apparatus according to claim 1 wherein said photo detectors of said array each comprise a photo diode.

10. The apparatus according to claim 1 wherein the reflected light received at said photo detectors is converted to an electrical signal, digitized and stored in a corresponding frame memory location.

11. The apparatus according to claim 1 wherein each of said photo detectors comprise a color filter, said color filters configured to limit the response of each detector to a narrow band of wavelength.

12. The apparatus according to claim 11 wherein said color filters are configured to be mechanically changed.

13. The apparatus according to claim 11 wherein said color filters are configured to be changed electro-optically.

14. The apparatus according to claim 1 wherein a grating is configured to direct light of different wavelengths toward different ones of said photo detectors have.

15. A trans-illumination imaging system comprising:
   two or more lasers configured to sequentially turn on to emit different wavelengths of light for a respective frame, said different wavelengths configured to determine a characteristic of the object;
   a beam combiner configured to combine said sequentially projected beams of light from said two or more lasers to produce a sequenced multispectral beam of light;
   a biaxial moving mirror, said moving mirror configured to direct said sequenced multi-spectral beam of laser light at the object along a plurality of optical paths, to produce a two-dimensional projection pattern;
   an array of photo detectors distributed around the object to have each respective field of view (FOV) not be along said plurality of optical paths, said array of photo detectors configured to detect said sequential frames of multispectral light reflected off of the deep internal structure of the object;
   a memory, said memory configured to receive and store said reflected multi-spectral frames of output by said array of photodetectors within corresponding memory locations;
   a projection laser configured to receive said photodetector output from said memory and to selectively project a beam of light at a visible wavelength to reveal the characteristic, said visible wavelength of said projection laser being different than said emitted wavelengths of light from said two or more lasers, said beam combiner configured to receive and combine said beam of visible light from said projection laser with said sequenced multispectral beam of light;
   a comparator configured to receive the output of said photo detectors, and to provide one bit of data for each pixel of the photo detector output to indicate whether each pixel brightness is above or below a comparator threshold value, said bit of pixel brightness data being stored in said memory and being updated for each said frame; said stored pixel brightness data used to adjust power to said laser on a pixel-by-pixel basis for each said frame to provide improved contrast sensitivity for said projection of the revealed characteristic.

16. The trans-illumination imaging system according to claim 15, further comprising means for wireless communication of the output of each said photo detector to said system.

17. The trans-illumination imaging system according to claim 16, further comprising an amplifier, said amplifier configured to receive the output of said photodetectors and to supply said output to said comparator.

18. The trans-illumination imaging system according to claim 17, further comprising a respective optical element for each said photo detector of said array, said respective optical elements configured to shape a field of view (FOV) of said respective photo detector.

19. The trans-illumination imaging system according to claim 18, wherein said array of photo detectors comprises a ring of uniformly distributed photodetectors.

20. The trans-illumination imaging system according to claim 19, wherein said amplifier is DC coupled, with bias of said DC coupling configured to compensate for changes in ambient room lighting.

21. The trans-illumination imaging system according to claim 20, wherein said two or more lasers and said projection laser comprises six lasers configured to project light at wavelengths of 460 nm, 525 nm, 540 nm, 577 nm, 650 nm, and 970 nm, to be configured to detect both bruising and erythema.

22. The trans-illumination imaging system according to claim 21 further comprising a second projection laser configured to project a beam of light at a second visible wavelength, said second visible wavelength being different from said emitted wavelengths of light of said two or more lasers and being different from said first visible wavelength of light from said first projection laser; and wherein said projected image comprises projection of said first and second visible wavelengths using a color map, wherein each of said two or more wavelengths comprises a color configured to represent a different characteristic.

23. The trans-illumination imaging system according to claim 15 wherein said two or more wavelengths emitted by said two or more lasers comprise two or more hyper-spectral wavelengths of light.

24. A trans-illumination imaging system, for use in capturing a multispectral image of a deep internal structure of an object with reduced noise from surface reflections, to produce a high contrast-ratio image of deep internal structure using high laser power, said trans-illumination imaging system comprising:
means to transmit a beam of light comprising two or more different wavelengths;
means to scan said beam of light in a first direction and in a second direction, with a first maximum angle between said beam of light at a beginning and an end of said first scan direction, and with a second maximum angle between said beam of light at a beginning and an end of said second scan direction, to scan said beam of light along a plurality of optical paths in a two dimensional scan pattern upon the object;
an array of photo detectors;
an optical element for each said photo detector, each said optical element configured to restrict a respective field of view (FOV) of each said photo detector;
a memory;
a comparator, said comparator configured to receive said output of said photo detectors, and to provide one bit of data for each pixel of the photo detector output to indicate whether each pixel brightness is above or below a comparator threshold value, said bit of pixel brightness data being stored in said memory and being incrementally updated for said selective projection, said stored pixel brightness data used to adjust power to said means to transmit light, on a pixel-by-pixel basis, for said selective projection to provide improved contrast sensitivity for said projected image;
wherein said first maximum angle of said scan pattern is configured so that said scanned light falls on a substantially small portion of the object in the first direction, and said restricted FOV of each said photo detector is not aligned with said plurality of optical paths of said scan pattern; and
wherein each said restricted FOV photo detector is thereby configured to detect said scanned two or more wavelengths of light after being differentially absorbed by the internal structure and the surrounding areas, with reduced noise from surface reflections; each said photo detector further configured to output a signal of a contrast formed by the absorption spectrum of said two or more wavelengths by the internal structure, with said means to transmit further configured to project one or more visible wavelengths of light, and by using said output signal from said photodetectors, to selectively project said contrast onto the surface of the object.

25. The trans-illumination imaging system according to claim 24, wherein said photo detectors of said array and each said respective FOV are configured to move synchronously about the object to remain unaligned with said plurality of optical paths of said scan pattern.

26. The trans-illumination imaging system according to claim 24, wherein said array of photo detectors comprises a ring of said photo detectors uniformly distributed around the object.

* * * * *